US005907016A

United States Patent [19]
Velander et al.

[11] Patent Number: 5,907,016
[45] Date of Patent: May 25, 1999

[54] METHOD OF COUPLING LIGANDS ONTO SUPPORTS AND PRODUCTS PRODUCED THEREFROM

[75] Inventors: William H. Velander, Blacksburg, Va.; Dean S. Milbrath; Anuradha Subramanian, both of St. Paul, Minn.

[73] Assignees: Virginia Tech Intellectual Properties,Inc., Blacksburg, Va.; Minnesota Mining and Manufacturing Company, St. Paul, Minn.

[21] Appl. No.: 08/296,588

[22] Filed: Aug. 29, 1994

Related U.S. Application Data

[63] Continuation of application No. 08/038,645, Mar. 29, 1993, abandoned.

[51] Int. Cl.$^6$ .......................... C07K 17/04; C07K 17/06; C07K 17/10; C07K 17/12
[52] U.S. Cl. .................... 525/54.1; 525/54.11; 525/54.2; 525/54.21; 525/54.23; 530/402
[58] Field of Search .............................. 525/54.1, 54.11, 525/54.2, 54.21, 54.23, 326.1; 530/402, 403, 405, 406

[56] References Cited

U.S. PATENT DOCUMENTS

| | | | |
|---|---|---|---|
| 4,704,366 | 11/1987 | Juarez-Salinas et al. | 436/501 |
| 4,775,714 | 10/1988 | Hermann et al. | 525/54.1 |
| 4,791,069 | 12/1988 | Hovorka et al. | 436/533 |
| 4,822,747 | 4/1989 | Johnson et al. | 436/532 |
| 4,839,419 | 6/1989 | Kraemer et al. | 525/54.1 |
| 4,968,742 | 11/1990 | Lewis et al. | 525/54.11 |
| 5,120,833 | 6/1992 | Kaplan | 530/356 |
| 5,200,471 | 4/1993 | Coleman et al. | 525/326.9 |
| 5,219,749 | 6/1993 | Bouriotis et al. | 435/227 |

FOREIGN PATENT DOCUMENTS

| | | |
|---|---|---|
| 0 392 783 | 10/1990 | European Pat. Off. . |
| 0 463 520 A1 | 1/1992 | European Pat. Off. . |
| 0 565 978 A1 | 10/1993 | European Pat. Off. . |
| WO 79/00541 | 8/1979 | WIPO . |
| WO 89/07618 | 8/1989 | WIPO . |
| WO 92/07879 | 5/1992 | WIPO . |
| WO 93/06925 | 4/1993 | WIPO . |

OTHER PUBLICATIONS

Coleman et al., "Effect of polyanionic salts on immobilization of protein A and antibody on azlactone–functional beads", *FASEB Journal*, vol. 5, No. 4, p. A805, (Mar. 11, 1991).

Coleman et al., "Immobilization of protein A at high density of azlactone–functional polymeric beads and their use in affinity chromatography", *Journal of Chromatography*, vol. 512, pp. 345–363 (Jun., 1990).

Hermanson et al., "Preparation and Use of Affinity Support on Azlactone–Activated, 3M EMPHAZE™ Biosupport Medium", *Journal of Molecular Recognition*, vol. 6, No. 1, p. 5 (Mar. 1993).

Bochert et al., "Improved Biocatalyst Effectiveness by Controlled Immobilization of Enzymes", Biotechnology and Bioengineering, vol. 26, pp. 727–736 (Jul., 1984).

Dennis et al., "Immobilization of Enzymes in Porous Supports: Effects of Support–Enzyme Solution Contacting", Biotechnology and Bioengineering, vol. 26, pp. 892–900 (Aug., 1984).

Lasch et al., "Studies of the Distribution of Proteins Bound to CNBr–Activated Sepharose 6B at the Electron–Microscopic Level", Eur. J. Biochem., vol. 60, pp. 163–167 (Dec., 1975).

Tharakan et al., "Effect of feed flow–rate, antigen concentration and antibody density on immunoaffinity purification of coagulation factor IX", Journal of Chromatography, vol. 522, pp. 153–162 (Nov. 28, 1990).

Stage et al., "Covalent Binding of Molecules to CNBr–Activated Agarose: Parameters Relevant to the Activation and Coupling Reactions", Biocimica et Biophysica, vol. 343, pp. 382–391 (Apr. 27, 1974).

Velander et al., "The Use of Fab–Masking Antigens to Enhance the Activity of Immobilized Antibodies", Biotechnology and Bioengineering, vol. 39, pp. 1013–1023 (Apr., 1992).

*Primary Examiner*—Jeffrey Mullis
*Attorney, Agent, or Firm*—Sughrue, Mion, Zinn, Macpeak & Seas, PLLC

[57] ABSTRACT

A method is disclosed for coupling a ligand within a porous support. The method involves mixing ligand and porous support under conditions sufficient to suppress coupling conditions of the ligand to the porous support while enhancing the relative rate of diffusion, to the rate of reaction, of the ligand into and within the porous support, and then altering the conditions to enhance rapid coupling of the ligand within the porous support. The alteration from diffusion conditions to coupling conditions involves a change in the reaction solution of pH, ionic strength, temperature, coupling competitor, such that a relatively lower Thiele Modulus during diffusion conditions changes to a relatively higher Thiele Modulus during coupling conditions. Derivatized porous supports produced according to the method are also disclosed. The derivatized porous support has enhanced functional efficiency. Derivatized porous supports prepared from azlactone-functional porous supports are also disclosed.

57 Claims, 2 Drawing Sheets

METHOD OF COUPLING LIGANDS ONTO SUPPORTS AND PRODUCTS PRODUCED THEREFROM

This is a continuation of application Ser. No. 08/038,645 filed Mar. 29, 1993, abandoned.

FIELD OF THE INVENTION

This invention relates to an improved method of covalently immobilizing ligands to supports and products produced from the method.

BACKGROUND OF THE INVENTION

The use of biologically active substances, such as proteins, is enhanced when such substances are covalently immobilized, i.e., coupled as ligands, onto supports. Separation techniques such as affinity chromatography are based on the ability of the coupled ligand to bind specific, targeted biologically active substances from a mixture of other materials. Common examples of affinity chromatography techniques include the binding of immunoglobulins using coupled proteins and the binding of antigens using coupled antibodies.

Successful ligand coupling is based on two factors: quantity immobilized and quality of immobilization. Quantity immobilized, expressed as density per unit volume of support, is an indicator of the amount of ligand coupled regardless of the quality of that immobilization. In fact, most protein coupled in highly dense regions of a support is biologically inactive. That is a waste.

Quality of immobilization, expressed as bound specific biological activity, is an indicator of the amount of ligand coupled onto a support in a manner that causes the ligand to retain its biologically activity. Maximizing bound specific biological activity is desirable. However, there must be enough ligand density to achieve practical utility.

The optimal condition in ligand coupling would be the maximum amount of ligand that is coupled with maximum bound specific biological activity. That results in optimal ligate binding or functional efficiency of the coupled ligand on the support.

Thus, for purposes of this application, "functional efficiency" means the combination of acceptable quantity of ligand coupling with acceptable bound specific biological activity.

Most ligand candidates are large molecules that have specific conformations necessary to retain biological activity. In the case of antibody binding of antigen, low antigen binding efficiencies have been attributed to the concerted actions of surface density of antibody, multi-point attachment of antibody to porous supports, undesirably restrictive conformations imposed by covalent attachment, steric effects, and orientation effects. See Velander et al., "The Use of Fab-Masking Antigens to Enhance the Activity of Immobilized Antibodies", *Biotechnology and Bioengineering*, Vol. 39, 1013–1023 (1992) which discloses how enhanced functional efficiency was achieved when the Fab portion of a monoclonal antibody was masked with synthetic antigens prior to covalent immobilization of the antibody on the support, followed by unmasking.

Enhanced bound specific biological activity was disclosed in PCT Publication WO 92/07879 (May 14, 1992) by the use of polyanionic salts in concentrations of greater than about 0.5M during covalent immobilization of biologically active materials to azlactone functional supports. Preferably, in addition to polyanionic salts, amounts of azlactone quencher were added during covalent immobilization to compete with the biologically active material during covalent immobilization.

Notwithstanding these advances in the field of ligand coupling technique, there remains the problem of optimizing functional efficiency of coupling expensive and precious biologically active substances as ligands to supports.

The problem of optimal functional efficiency has not been solved by others. For example, U.S. Pat. No. 4,968,742 (Lewis et al.) uses an elaborate, stepwise method to couple ligands involving derivatizing a polymer with an activating agent to introduce a couplable functional group, with the derivatization performed in the presence of a blocking agent which is reactive with the same functionality on the polymer as the activating agent, in order to control the number of couplable functional groups for covalent immobilization of ligand.

U.S. Pat. No. 4,839,419 (Kramer et al.) discloses a method for adsorbing a protein onto a support and then crosslinking the protein to the support where the reaction conditions for coupling do not differ from those of the adsorption.

U.S. Pat. No. 4,775,714 (Hermann et al.) discloses a two-step process of immobilization of biologically efficient compounds on a carrier involving the steps of hydrophobic interaction and covalent immobilization. Examples 5–7 therein disclose the stepwise addition of a solution of inorganic salt, in a concentration of between 0.5 M to 3.0 M, to a reaction vessel containing the biologically efficient compound and the carrier, followed by a slow reaction (40 hours at 40° C. under moderate shaking) in order to produce an immobilized, biologically active compound.

There have been efforts to experimentally determine how coupled protein was distributed to activated porous supports. See Stage et al. *Biochimica et Biophysica* 343, 382–391, (1974), where uniform distribution was reported for immunoglobulins coupled to cyanogen bromide-activated Sepharose branded beads. See also, Lasch et al. *Eur. J. Biochem.* 60, 163–167 (1975) which reported that uniform distributions of ferritin were found, except when the CNBr activation of Sepharose branded beads was very high (>50 mg/ml) and/or when coupling efficiency was higher than 90%. Thus, non-uniform distribution resulted from high coupling efficiencies.

While non-uniform distribution of immobilized enzymes on porous supports has been studied using alterations in reaction conditions, and, in some cases, found preferable, others have warned of the possibility that non-uniform antibody immobilization on Sepharose branded beads was responsible for the loss of binding activity with increase of average antibody density. See Tharakan et al. *J. Chrom.* 522, 153–162 (1990).

Another sought to improve the performance of an immobilized enzyme by "kinetic control" during the immobilization by using salt concentration and time to control the enzyme distribution to an ionic support and chemically couple with a reagent added to fix this distribution. See Borchert et al. *Biotechnology and Bioengineering* (26)7, 727–736 (1984). Another has studied reaction conditions and proposed a restriction effect at openings of pores in the porous support that could prevent further protein from being coupled to the support. See Clark et al. *Biotechnology and Bioengineering* 26(8) 892–900 (1984).

Generally, the art has found that one can achieve coupling efficiency by reacting at conditions to achieve a high coupling capacity at the expense of loss of bound specific biological activity. Alternatively, the art has found that one can achieve high bound specific biological activity with lower coupling efficiency (because the total amount of ligand coupled is lowered.) In both of these circumstances, the reaction conditions were not altered during the reaction process except as described in U.S. Pat. No. 4,775,714 (Hermann et al.) in Examples 5–7. In that circumstance, salt was added stepwise after the ligand solution and the support were combined but before the reaction commenced for 40 hours at 40° C.

SUMMARY OF THE INVENTION

The present invention provides a rapid method of covalent immobilization that surprisingly enhances functional efficiency of a biologically active substance as a ligand coupled to surfaces within a porous support. The method effectively distributes the ligand within a support prior to coupling of the ligand onto the support. The method employs a two-step coupling process where reaction conditions are altered between steps, and preferably where no immobilization agent is added between steps.

As a result, the support derivatized with the ligand optimizes functional efficiency with a targeted biologically active substance.

The first step of the method suppresses conditions or other reaction between ligand and a porous support, which enhances the relative rate of diffusion, to the rate of reaction, of the ligand into and within the support. The second step of the method enhances coupling conditions, such that the ligand couples to the support rapidly, i.e., within about four hours so that the ligand couples to the support before the ligand has an opportunity to vacate the desired location for coupling.

The method achieves a ligand coupling that avoids surface crowding that would otherwise inhibit or lower the biological activity of the ligand. Coupled ligand on a derivatized support prepared using the method of the present invention is remarkably more uniformly spatially distributed than a derivatized support using previously known methods. The resulting derivatized support achieves about a 1.25-fold to 10-fold increase in functional efficiency than seen when previously known coupling methods have been employed.

A feature of the present invention is the ease of ligand coupling in a manner that optimizes functional efficiency.

Another feature of the present invention is the increased efficiency of use of precious or expensive biologically active substances such as ligands for coupling onto a support.

An advantage of the present invention is a dramatic reduction of the amount of derivatized support needed to achieve a given biochemical processing capacity provided by the immobilized biologically active substance for any given amount of ligand coupled per volume of support. Conversely expressed, the advantage is that the use of a given amount of derivatized support prepared according to the present invention will dramatically increase the biochemical processing capacity. Either way, dramatic improvement to biochemical processing capacity is realized by the present invention.

Another advantage of the present invention is the savings in related costs (e.g., the expense of processing fluids such as aqueous buffers) of biochemical processing capacity due to the unexpectedly enhanced functional efficiency of the derivatized support.

Another advantage of the present invention is that the method provides a more uniform spatial distribution of ligand coupled to support. This advantage results in a decrease in spatial density of ligand coupled to the support, making greater use of electrophilic functionality residing at the surfaces of the support. This advantage also permits a larger average density of ligand coupled to the support with increased amounts of ligand, without overcrowding of ligand at or near the exterior surfaces of the support.

Thus, the invention provides a method for coupling a ligand within a porous support that comprises the steps of mixing ligand and porous support under conditions sufficient to suppress coupling of the ligand to the porous support while enhancing the relative rate of diffusion, to the rate of reaction, of the ligand into and within the porous support, and altering conditions to enhance rapid coupling of the ligand within the porous support.

In another aspect of the invention, the method improves functional efficiency of binding a ligate otherwise deleteriously affected by restricted diffusion into a porous support or by steric effects of binding to a ligand coupled to the porous support. The steps of the method comprise coupling a ligand to the porous support according to the two-step diffusion/coupling method indicated above, whereby spatial distribution of ligand coupled to surfaces of the supports enhances functional efficiency of ligates otherwise affected by restricted diffusion or steric effects, and binding the ligate to the spatially distributed ligand, such that functional efficiency of the ligand is greater than the functional efficiency of the ligand coupled in circumstances where either restricted diffusion into the porous support, or steric effects of the ligate binding, or both, are present.

The invention also provides a derivatized porous support produced according to the method of the present invention.

The invention also provides a derivatized porous support comprising Protein A coupled to the porous support in a coupling efficiency of at least about 80% and having a functional efficiency relative to binding immunoglobulins of greater than about 3.0 bound IgG/coupled Protein A. It is contemplated that an increase of greater than 15% functional efficiency can be achieved at coupling densities of from about 6 mg to about 15 mg of Protein A coupled per ml of swollen or hydrated support.

The invention also provides a derivatized porous support comprising an antibody against ligate protein (e.g., Protein C) coupled to the porous support in a coupling efficiency of greater than about 70% and having a functional efficiency relative to binding ligate protein (e.g., Protein C) to the coupled anti-ligate protein (e.g., Protein C antibody) of greater than about 20% at a molar ratio of 2:1 of ligate protein to antibody. It is contemplated that greater than 15% functional efficiency can be achieved at coupling densities of from about 3 mg to about 10 mg of antibody coupled per ml of swollen or hydrated support.

The invention also provides a derivatized porous support comprising ligand coupled to the porous support in a manner that at least 30% of the amount of coupled ligand is coupled to internal surfaces, i.e., those surfaces that are within 70% of the geometric center of the support. Expressed alternatively for a spherical particle, the internal surfaces are those surfaces within a sphere having a radius of 70% of the total radius of the particle.

The invention also provides a derivatized porous support comprising ligand coupled to the porous support in a manner that has a percentage of permeation of coupled ligand of about 30% to the internal surfaces of a porous support.

For a greater appreciation of the invention, embodiments of the invention are described following a Brief Description of the Drawings.

EMBODIMENTS OF THE INVENTION

Porous Supports

Acceptable porous supports for use in the present invention include those commercially available for affinity chromatography techniques. The porous support can be any porous solid, whether natural or synthetic, organic or inorganic, having a porous structure and which is insoluble in water or aqueous solutions. Suitable solids with a porous structure have pores of an average diameter of at least 30 nanometers and a pore volume of over 0.1 $cm^3/g$. Preferably, the average pore diameter is at least 50 nm because larger pores will be less restrictive to diffusion. Preferably, the pore volume is at least 0.5 $cm^3/g$ for greater potential capacity due to greater surface area surrounding the pores.

Nonlimiting examples of such porous supports are naturally or synthetically-modified natural compositions such as polysaccharides, celluloses, and agaroses. An example of a commercially available agarose is Sepharose branded beads from Pharmacia AB of Uppsala, Sweden. Such porous supports require activation with a composition, such as cyanogen bromide or cyanotransfer agents, in order to covalently immobilize ligands. Such activation is required prior to using the method of the present invention.

Other nonlimiting examples of such porous supports are synthetic homopolymers and copolymers of acrylates, methacrylates, acrylamides, vinyl aromatics, and vinyl alcohols. Desirably, such homopolymers or copolymers have a functionality (e.g., azlactone, aldehyde, or the like) or are modified to provide a functionality to permit rapid, direct covalent reaction with ligands to form derivatized supports. Oxirane or epoxide functionality is not suitable for methods of the present invention because such groups are not rapid in coupling reaction or require adversely high pH for rapid coupling. See Yarmush et al., *Biotech Adv.* 10, 413–446 (1992). As seen in Example 5 of U.S. Pat. No. 4,775,714 (Hermann et al.), the coupling reaction time was 40 hours at 40° C. under moderate shaking. That is not a rapid coupling condition, i.e., within about four hours.

Other nonlimiting examples of such porous supports are porous inorganic particles such as porous glass, silica, alumina, zirconium oxides, and other metal oxides.

Porous supports can be membranes, porous fibers, webs, or particles, such as beads. Preferably, porous supports useful in the present invention are reactive porous particles so that the ligand can be covalently coupled to the support.

In addition to these supports described above that require activation prior to use according to the present invention, other supports have covalently reactive surfaces without need for an intermediate activation step. Preferably, such directly reactive porous supports are particles.

Directly reactive porous particles useful in the present invention are generally of two broad types: chemically modified inorganic particles and organic, polymeric particles.

The inorganic particles may be, for example, metal oxides such as alumina, silica, and zirconia; glass beads, glass bubbles, and controlled pore glass; and the like. These particles are chemically modified by methods such as coating with a polymer (usually organic) which contains a reactive functional group or by reaction with a suitable reagent (e.g. an alkoxy silane coupling agent) containing the reactive functional group.

The organic particles may be crosslinked or non-crosslinked polymers which have been prepared, for example, by polymerization or copolymerization of a monomer containing the appropriate reactive functional group, by coating a particle support as described above, or by chemical modification of another polymer to introduce the reactive functional group.

A number of useful particles are commercially available or can be prepared by techniques well known in the art, a partial listing of which can be found below in Table 1.

Directly reactive particles useful in the present invention can have a spherical shape, a regular shape, or an irregular shape. Size of reactive particles can vary widely within the scope of the invention and will depend to some extent upon the intended use of the particles.

Generally size of reactive particles ranges from 0.1 micrometers to 5 millimeters in average diameter.

Whether directly covalently reactive or indirectly activated via a composition such as cyanogen bromide, the covalent reactive functional groups which are useful for the purposes of the invention can be classified in general as electrophiles. Reaction with a nucleophile (e.g. amine, alcohol, or mercaptan) produces a covalent chemical bond either by an addition reaction or by a displacement or substitution type reaction (in which a byproduct molecule is released). Addition type reactions are preferred.

Examples of useful directly and indirectly reactive functional groups and examples of commercially available particles containing them are listed in Table 1.

TABLE 1

Functional Groups and Porous Particles

| Functional Group | Trade Name | Supplier | Type |
|---|---|---|---|
| N-Hydroxysuccinimide Esters: | Affi-Gel ™ | BioRad | Agarose |
| | Affi-Prep ™ | BioRad | Organic polymer |
| Sulfonyl Esters: | Tresyl Activated Agarose | Pierce | Agarose |
| | Tosyl Activated Agarose | Pierce | Agarose |
| Iodoacetyl: | SulfoLink ™ | Pierce | Agarose |
| Aldehyde: | AminoLink ™ | Pierce | Agarose |
| Imidazolyl Carbamate: | Reacti-Gel ™ | Pierce | Agarose Acrylamide Copolymer Silica |

TABLE 1-continued

Functional Groups and Porous Particles

| Functional Group | Trade Name | Supplier | Type |
|---|---|---|---|
| Cyanogen Bromide: | CNBr-activated Sepharose ™ | Pharmacia | Agarose |

Particularly preferred as reactive particles useful in the present invention are particles having azlactone-functional groups on internal and/or external surfaces of such particles. Thus, such reactive particles have an azlactone-functional group of Formula I:

I wherein:

$R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

Azlactone-functional reactive particles are particularly preferred in the present invention because such particles rapidly and directly covalently couple ligands better than commercially available reactive functional groups shown in Table 1. Further, such azlactone-functional groups are quite stable prior to covalent coupling with a ligand. Further, covalent coupling of a ligand with an azlactone-functional group causes no displacement of a byproduct molecule, which avoids undesired purification of the composite article after covalent coupling of the ligand.

Also, azlactone-functional groups are known to possess high covalent coupling capacities with biologically active materials such as Protein A. Further, such high covalent coupling capacities with Protein A also yield high specific bound biological activity of Protein A as the coupled ligand. Thus, an azlactone-functional reactive particle is particularly preferred for use in the present invention.

Azlactone-functional polymeric particles can be made, for example, by copolymerization of a (meth)acryloylamino acid with a variety of other free radically polymerizable comonomers followed by reaction with a cyclizing agent, as described in U.S. Pat. Nos. 4,737,560 and 4,871,824, which are incorporated herein by reference, or by copolymerization of an alkenyl azlactone with other comonomers as described in assignee's copending patent application U.S. Ser. No. 158,258, filed Feb. 19, 1988, or in counterpart European Patent Publication 0 392 735, which are both incorporated herein by reference. Azlactone-functional particles can also be prepared by solution coating an azlactone-functional polymer onto an organic or inorganic particle, also as described in above mentioned European Patent Publication 0 392 735.

Azlactone-functional reactive particles can also be made from azlactone graft copolymers which are disclosed in U.S. Pat. No. 5,013,795 and European Patent Publication 0 392 783, the disclosures of which are incorporated by reference.

Size of particles of azlactone-functional particles can be from about 0.1 to 1,000 micrometers and preferably from 0.5 to 250 micrometers. Dry azlactone-functional particles can have an average pore size ranging from about 1 to about 300 nanometers and preferably from 5 to about 200 nanometers. Azlactone-functional particles can have an average pore volume of at least 1.0 cm$^3$/g of particle. In a particle having a size of 50–80 micrometers, a pore volume of at least 1.2 cm$^3$/g provides a pore volume of about 60% of the particle volume. In the same particle, the surface area is at least 50 m$^2$/g. Thus, there is substantial surface area within an azlactone-functional particle available for covalent immobilization according to the present invention.

Most preferably, porous supports useful for the present invention are Emphaze™ brand porous azlactone-functional activated affinity chromatography beads commercially available from Minnesota Mining and Manufacturing Company of St. Paul, Minn.

Ligands for Covalent Immobilization

As stated above, reactive functional groups on porous supports are desirably electrophiles. Thus, for direct covalent immobilization, ligands useful in the present invention contain nucleophiles.

Nonlimiting examples of ligand functional groups include primary and secondary amines, alcohols, and mercaptans. Of these, amine-functional ligands are especially preferred.

Ligands useful for the preparation of adduct composite articles can also vary widely within the scope of the present invention. Preferably, a ligand is chosen based upon the contemplated end use of the derivatized porous support.

Once ligands are coupled according to methods of the present invention, such ligands are available for biological or chemical interaction with an enhanced functional efficiency, such as adsorbing, complexing, catalysis, or reagent end use.

Derivatized porous supports are useful as adsorbants, complexing agents, catalysts, reagents, as enzyme and other protein-bearing supports, and as chromatographic articles.

In a preferred aspect of the present invention, the ligand desired for covalent immobilization is a biologically active substance or compound having nucleophilic-functional groups. Nonlimiting examples of biologically active materials are substances which are biologically, immunochemically, physiologically, or pharmaceutically active. Examples of biologically active materials include proteins, peptides, polypeptides, antibodies (monoclonal or polyclonal), antigenic substances, enzymes, cofactors, inhibitors, lectins, hormones, receptors, coagulation factors, amino acids, histones, vitamins, drugs, cell surface markers, and substances which interact with them.

Of the biologically active materials, proteins, enzymes and antigenic substances are desired for covalent immobilization. Nonlimiting examples of proteins, enzymes, and antigenic substances include natural and recombinant Protein A (ProtA), Immunoglobulins such as rat (rIg), human (hIg), bovine (bIg), rabbit (rbIg), and mouse (mIg), Concanavalin A (ConA), Bovine Serum Albumin (BSA), Thyroglobulin (TG), Apoferritin (Af), Lysozyme (Ly), Carbonic Anhydrase (CA), and Bacterial Antigen (BA). Nonlimiting examples of coagulation factors include Protein C (ProtC), heparin, fibrinogen, and thrombin.

Uses for coupled proteins, enzymes and antigenic substances are disclosed in European Patent Publication 0 392 735. Uses for coagulation factors include activation of zymogens to active proteins, such as Protein C to Active Protein C by coupled thrombin.

The presently preferred biologically active substances are antibodies and ProtA.

Alternatively, a derivatized porous support of the present invention can comprise a coupled enzyme to catalyze a chemical transformation of substances recognized by the enzyme. Also, a derivatized porous support comprising a coupled antigenic substance can be utilized for affinity purification of a corresponding antibody from a complex biological fluid.

In another example, porous particles having Protein A coupled to internal and external surfaces according to the method of the present invention can adsorb biologically active materials such as Immunoglobulin G for affinity separations processes. In another example, a derivatized porous support can be used for immobilization of antibodies or be used for immunodiagnostics or for Western blotting.

Presently preferred azlactone-functional groups will undergo nucleophilic attack by amines, thiols, and alcohols. Thus, ligands having at least one amine, thiol, or alcohol group thereon are candidates for covalent immobilization in an azlactone-functional porous support.

The method of the present invention is particularly useful for binding large ligates that are otherwise affected by restricted diffusion into a porous support or by steric effects of binding to a densely coupled ligand, or both.

Without being limiting, large ligates can be characterized as those ligates which would be unable to traverse a pore already having ligate bound to coupled ligand at opening surfaces of the pore. Thus, coupled ligand within the derivatized support are under-utilized or possibly un-utilized during binding if opening surfaces of the pore coupled with ligand bind ligates and block passage to derivatized surfaces within the porous support.

Also, large ligates can be characterized as those ligates which adversely alter the binding of additional ligates due to steric effects. Thus, binding of the ligate can occur but inefficiently (e.g., in a manner that causes a waste of coupled ligand). If that ligand were more uniformly spatially distributed, the support could accommodate both a greater binding capacity and a greater functional efficiency.

The "largeness" of the ligate is a relative consequence of the pore size of the porous support, the reactivity and density of coupled ligand, and other factors. Nonlimiting examples of large ligates are those biologically active materials identified above as ligand candidates, except for small molecules such as peptides, polypeptides, amino acids, and drugs.

Method of Covalent Immobilization

The method of the present invention involves two steps. The first step brings the ligand in close proximity to surfaces of the porous support. The second step causes rapid covalent immobilization, i.e., coupling within about four hours, of the ligand to surfaces of the porous support. An advantage of the present invention is the superior functional efficiency achieved by coupling ligands according to the method of the present invention.

The first step employs, in a single reaction vessel, conditions sufficient to suppress coupling of ligand to the support while enhancing the relative rate of diffusion, to the rate of reaction, of the ligand into and within the porous support. Thus, the first step suppresses the rate of ligand coupling relative to the rate of ligand diffusion.

Nonlimiting examples of suppressing coupling conditions in the reaction vessel include use of specific ranges of conditions in one or more of a combination of pH, ionic strength, temperature, and coupling competitors.

Presently preferred as conditions to suppress coupling are a control of pH of a reaction solution and/or control of ionic strength, in which the ligand and the porous support are mixed and otherwise in condition for coupling. The pH can be controlled to be in a range from about 3 to about 7. A pH of that range provides diffusion conditions that minimize the reaction of a nucleophilic group on a ligand with an electrophilic group on the surface of a porous support.

More preferably, the pH during diffusion should be from about 4 to about 6 because of the stability of the electrophilic functional groups to hydrolysis is greater as pH increases.

Most preferably, the pH during diffusion is about 5, because electrophilic functional groups are more stable to possible hydrolysis.

When pH of the reaction solution ranges from about 3 to about 7, other reaction conditions can be as conventionally employed in the art of immobilization. In other words, adjustment of the pH alone can be sufficient to suppress coupling conditions while also enhancing the relative rate of diffusion, to the rate of reaction, of the ligand into and within the porous support.

Ionic strength due to the presence of polyanionic salts (e.g., sulfates, phosphates, citrates, tartrates, and the like), during diffusion is minimized to suppress coupling conditions. Preferably, the molarity of the polyanionic salts in the reaction solution during diffusion is from about 0.01 to about 0.4 M.

Coupling competitors, described in greater detail below, which would otherwise compete for nucleophilic reaction with the functional groups can be 0 to 2 Molarity.

Temperature of the reaction solution during diffusion needs to be controlled to slow the reaction rate of ligand coupling. Preferably, the temperature can be from about the freezing point of the aqueous solution to about 25° C.

The reaction solution usually includes buffering agents. Buffering agents for aqueous media include acetate, phosphate, pyrophosphate, borate, and other salts known to those skilled in the art, such as those buffering agents disclosed in Good et al., *Biochemistry,* 5, (1966) p. 467 et seq. (the disclosure of which is incorporated by reference herein).

The concentration of buffering agents in aqueous media can range from about 10 mM to about 750 mM and desirably from about 50 mM to about 200 mM, inclusive, depending on the concentration of biologically active substance chosen for coupling and the concentrations of other optional ingredients that can affect the ionic strength of the reaction solution.

The duration of the first step should be sufficient in length to assure diffusion of the ligand into proximity with all surfaces of the porous support. The amount of time can vary according to the type of porous support employed, the pore size and pore volume of the porous support, the size and conformation of the ligand to diffuse through the pore volume of the porous support and other physical considerations. Generally, a diffusion duration of at least 5 minutes is sufficient to accomplish acceptable diffusion. Desirably, diffusion lasts at least 10 minutes to improve diffusion. Preferably, diffusion lasts at least 15 minutes to assure diffusion in most porous supports in the case of smaller support geometries. For larger support geometries, the diffusion lasts to at least the characteristic diffusion time, which is the mean support thickness divided by the diffusivity of the ligand of interest in aqueous solution.

The second step causes coupling of ligand to surfaces of the porous support to occur rapidly and assuredly. Thus, reaction conditions in the second step are abruptly altered from that of the first step and preferably occur in the absence of adding any coupling agent to the reaction solution. A "coupling agent" means a reagent that reacts with either the ligand or the support to improve the coupling of the ligand to the support but does not mean a coupling competitor, i.e., a reagent that competes for reaction sites on the porous support.

The rate of coupling is a function of the rate constant of coupling, the concentration of ligand, reactivity of the functional groups per unit area of the support, the rate of diffusion of ligand into the support, and the temperature.

When diffusion conditions are established using pH of the reaction solution, a change in pH comprises the second step. coupling conditions are enhanced when pH of a reaction solution is changed to a pH within one pKa of the nucleophilic ligand, usually within a range from about 7 to about 10. This range causes rapid and assured coupling of ligand to the porous support.

A pH of this range provides coupling conditions that maximize the reaction of a nucleophilic group on a ligand with an electrophilic group on the surface of a porous support.

More preferably, the pH of the reaction solution for coupling should be from about 7.5 to about 9.5 so that hydrolysis or other reaction with solvent is lessened.

Most preferably, the pH of the reaction solution for coupling is about 8.5 to maintain the biological activity of ligands, especially proteinaceous ligands.

The alteration in reaction conditions from the diffusion step to the coupling step can be limited to a change in pH or can also include other changes.

In addition to, or in substitution for a change in pH, a change in ionic strength of the reaction solution can also be used to enhance functional efficiency of the ligand coupled to the porous support. The amount of change in ionic strength can be in an amount sufficient to enhance coupling of ligand and to enhance functional efficiency of the coupled ligand.

The amount of change in ionic strength from the diffusion step to the coupling step can range from about 0.5M to about 1.5M. Preferably, the amount of change in ionic strength can range from about 0.6M to about 1.2M to maintain the solubility of ligands, especially proteinaceous ligands. Most preferably, the change in ionic strength of the solution in the coupling step can be about 1.0–1.2M.

The change in ionic strength is induced by an addition of polyanionic salt or salts to the reaction solution. Suitable polyanionic salts, both inorganic and organic, are identified in PCT WO 92/07879 (corresponding to copending, coassigned U.S. patent application Ser. No. 07/609,436 (Coleman et al.), now U.S. Pat. No. 5,200,471 the disclosure of which is incorporated by reference).

As explained in Coleman et al. regarding preferred azlactone-functional supports, using an inorganic polyanionic salt in aqueous buffered media to covalently immobilize protein to azlactone-functional polymeric supports more than doubles the bound specific biological activity of the biologically active material, when compared to using an inorganic monoanionic salt, such as NaCl.

This enhanced efficiency of immobilization is achieved in a very rapid and facile reaction. The use of an inorganic polyanionic salt in high concentrations does not disrupt other valued aspects of using azlactone-functional polymeric supports such as the very rapid covalent immobilization rates achievable at ambient temperatures.

Of the inorganic polyanionic salts, sulfates are desired because of increased bound specific biological activity relative to the molar concentration of inorganic polyanion in the aqueous media. If inorganic polyanionic salts are used, use of $Na_2SO_4$ is presently preferred when coupling proteins (that have activity unaffected by metallic cations) in an aqueous medium buffered at a pH from about pH 4 to about pH 9. Sulfates are also preferred to phosphates because a lower molar concentration of sulfates than phosphates is necessary to achieve the same density of coupled ligand on the azlactone-functional polymeric support. Evidence of this advantage may be found in Coleman et al. *J. Chromatogr.* 512 (1990) 345–363, which is incorporated by reference herein.

Preferably, organic polyacids and their salts can provide even more productive and efficient coupling of ligands on preferred azlactone-functional polymeric supports than inorganic polyanionic salts. Organic polyanionic salts are more consistently ionic than inorganic polyanionic salts in a pH range of pH 7 to pH 9 where most covalent immobilizations are conducted and in the preferred range of pH alteration from the diffusion step to the coupling step of the present invention. Thus, organic polyanionic salts have a higher ionic strength per mole of polyanion. Consequently, fewer moles of organic salt are frequently required for covalent immobilization. Further, a greater variety of organic polyanionic salts than inorganic polyanionic salts is sufficiently soluble in buffered aqueous media employed in covalent immobilizations. Thus, organic polyanionic salts are presently preferred to inorganic polyanionic salts.

Of the organic polyacid candidates, di-acids, tri-acids, and tetra-acids, or their salts are desired. Nonlimiting examples of salts of such acids include malonate, malate, and tartrate di-acid salts of alkali metals, citrate tri-acid and nitrilo-triacetic acid (NTA) salts of alkali metals, and ethylenediaminetetraacetic acid (EDTA) tetra-acid salts of alkali metals. The presently preferred organic polyanionic salt is sodium citrate.

In addition to, or in substitution for, a change in pH and/or a change in ionic strength, an addition of a coupling competitor to the reaction solution can also be used to enhance functional efficiency of the ligand coupled to the porous support.

The coupling competitor can be added in an amount sufficient to enhance bound specific biological activity of ligand (but not in an amount which substantially reduces the amount of ligand coupled) in a manner resulting in enhanced functional efficiency of the coupled ligand.

The type of coupling competitor can vary according to the nature of the ligand to be coupled to the porous support. The kinetics of reaction (as influenced by pH, ligand concentration, temperature, ionic strength of the reaction solution, among other factors) between the porous support and the ligand determine the amount and type of coupling competitor to be used.

While not being limited to a particular theory, a coupling competitor competes for the reactive sites on a porous support where ligand would otherwise couple. The reduction in the number of reactive sites can limit the possibility that ligand couples in a manner that alters its conformation and reduces or eliminates its biological activity. Unexpectedly, it is believed that a coupling competitor enhances functional efficiency of the coupled ligand by providing a sparcity of reactive sites without eliminating too many reactive sites for coupling. This also tends to result in a more uniform or effective distribution of coupled ligand.

When preferred azlactone-functional porous supports are used, coupling competitors are azlactone quenchers. Suitable azlactone quenchers are also identified in PCT WO 92/07879 (corresponding to copending, coassigned U.S. patent application Ser. No. 07/609,436 (Coleman et al.).

Nonlimiting examples of azlactone quenchers for use include ethanolamine, bovine serum albumin, casein lysate, hydroxylamine, ethylamine, ammonium hydroxide, glycine, ammonium sulfate, butylamine, glycinamide, TRIS, gelatin, lysozyme, non-fat dry milk, beta-mercaptoethanol, mercaptoethylether, dithiothreitol, glutathione, arginine, guanidine, lysine, diamines, and combinations thereof. Some of these nonlimiting examples include proteins "irrelevant" to the immobilization desired.

The concentration of azlactone quencher to be added with a change in pH and/or an increase of ionic strength for the second step of the method can range from about 0.1 M to about 10 M. Desirably, the range may be between about 0.5 M to about 2 M. When ethanolamine serves as azlactone quencher, the concentration may range from about 0.1 M to about 1 M. The presently preferred concentration of ethanolamine as azlactone quencher is about 0.5 M to about 1 M.

In addition to, or in substitution for, a change in pH, a change in ionic strength, or the addition of a coupling competitor, or a combination of them, an increase in the temperature of the reaction solution can also be used to enhance functional efficiency of the ligand coupled to the porous support. The amount of temperature change can be an amount sufficient to enhance coupling of ligand, so long as the speed of the reaction is rapid, and to enhance functional efficiency of the coupled ligand.

The temperature increase can be about 10° C. to about 35° C., and preferably about 20° C. to about 30° C. because an increase in temperature of that amount increases reactivity of the ligand to the support without deleteriously affecting the biological activity of the ligand.

While not being limited to a particular theory, one or more of an increase of pH, an increase in ionic strength, an increase of temperature, or an addition of a coupling competitor to the reaction solution causes ligand to couple in a manner which retains bound specific biological activity of the ligand due to a resulting more uniform or effective distribution of ligand which minimizes restricted diffusion or steric effects of ligates attempting to bind to the coupled ligand. This improves functional efficiency of the resulting coupled ligand by minimizing the number of coupled ligands that are not biologically active and maximizing the amount of ligand coupled.

Coupling during the second step is rapid and assured. The duration of the step can range from 0.5 to 4 hours.

Coupling is completed by quenching any remaining reactive sites with an addition, in excess, of a quencher that couples to effectively all of the remaining reactive sites on the porous support.

When the porous support is azlactone-functional, the quencher employed can be any of the azlactone quenchers identified above in concentrations in excess.

While not being limited to a particular theory, the method of the present invention utilizes the advantages of controlling the Thiele modulus during the diffusion and the coupling steps of the method.

Thiele modulus broadly expresses in dimensionless terms the ratio of the rate of reaction to the rate of diffusion and can be expressed using the following equation (I):

$$\phi = R_p (ka/D_e)^{1/2} \tag{I}$$

where $R_p$ is the Reactivity of the ligand, k is the first-order rate constant, a is the internal surface area, and $D_e$ is the effective Diffusivity of the ligand.

Another expression of Thiele modulus is the following equation (II):

$$\phi = 1/2(d_p)(V_{max}\rho/K_m D_e)^{1/2} \tag{II}$$

where $d_p$ is the carrier diameter, $V_{max}$ is the activity, $\rho$ is density, $K_m$ is kinetic parameter for coupling, and $D_e$ is effective Diffusivity. See Borchert et al. publication identified above.

The first step of the present invention is to suppress coupling conditions to enhance the relative rate of diffusion to the rate of coupling. The first step utilizes a lower Thiele modulus (where rate of diffusion is appreciably greater than rate of reaction) relative to the second step. Conversely, the second step utilizes a higher Thiele modulus (where rate of reaction is appreciably greater than rate of diffusion) than found in the first step.

Thus, expressed alternatively, the method of the present invention provides a permeation step for more uniform spatial distribution having conditions using relatively low Thiele modulus followed by a coupling step for rapid coupling which uses conditions having a relatively high Thiele modulus.

Relatively low Thiele modulus conditions are achievable with a low pH, low ionic strength reaction medium, lower temperature, coupling competitor, and combinations of them.

Relatively high Thiele modulus conditions are achievable with a high pH, high ionic strength reaction medium, higher temperature, coupling competitor, and combinations of them.

The impact of these factors upon Thiele modulus for ligand diffusion and coupling depends on the ligand chosen. For example, functional efficiency of Protein A coupled to an azlactone-functional bead can be enhanced with a change in Thiele modulus to initiate the coupling step using an increase in ionic strength, an addition of coupling competitor, a combination of those two factors. However, a change in pH alone will result in enhanced functional efficiency of anti-Protein C antibody on a porous azlactone-functional bead.

At any given ligand concentration range in solution, one of the results in controlling the difference in Thiele modulus between the first and second step is a change in the activation energy necessary for a coupling of ligand to a functional group on a surface within a porous support. The conditions of the lower Thiele modulus conditions raise the activation energy required for the coupling reaction, while the conditions of the higher Thiele modulus lower the activation energy required for the coupling reaction.

The abruptness of the step change in Thiele modulus conditions after the diffusion step and to initiate the coupling step of the method results in minimal back-diffusion of ligand from the support. This maintains much of the dispersed spatial distribution achieved during the diffusion step. Further, the reaction kinetics of the functional group on the surface of the porous support enhances the rapidity of the coupling reaction before the desired more uniform spatial distribution of the ligand within the support is lost. Rapidity of the coupling reaction should be less than about 4 hours and preferably less than about 1 hour.

Usefulness of the Invention

The method of the present invention provides a process of immobilizing biologically active substances on porous supports in such a fashion as to avoid surface crowding which inactivates a significant portion of the coupled ligand. The derivatized support has coupled ligand with a molecular sparcity which has a functional efficiency that is significantly higher than ligand coupled with a higher surface density.

Figure 1:
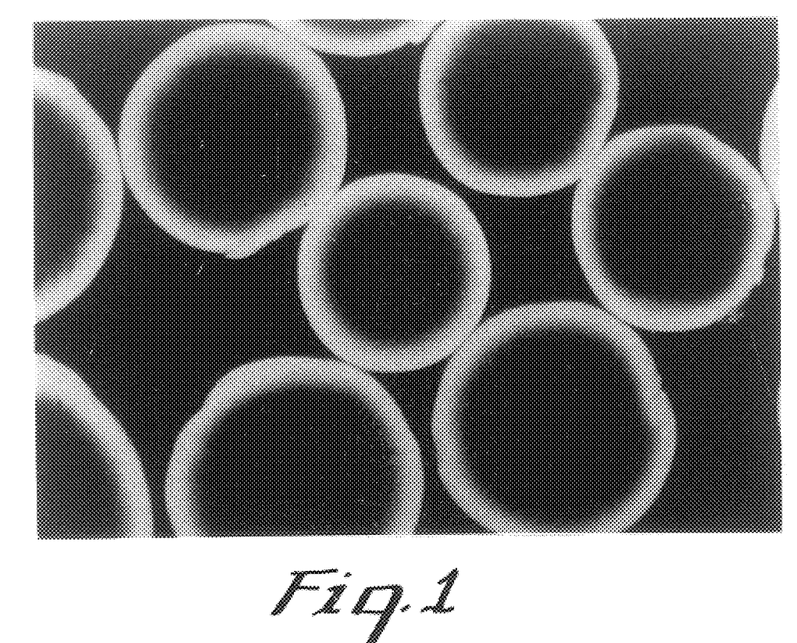
FIG. 1 is a comparison fluorescence micrograph of a derivatized porous support, shown in cross-section, produced according to prior art methods, that shows an uneven distribution of Protein A ligand coupled principally at outer surfaces of the support, demonstrating an undesired "halo effect".
Figure 2:
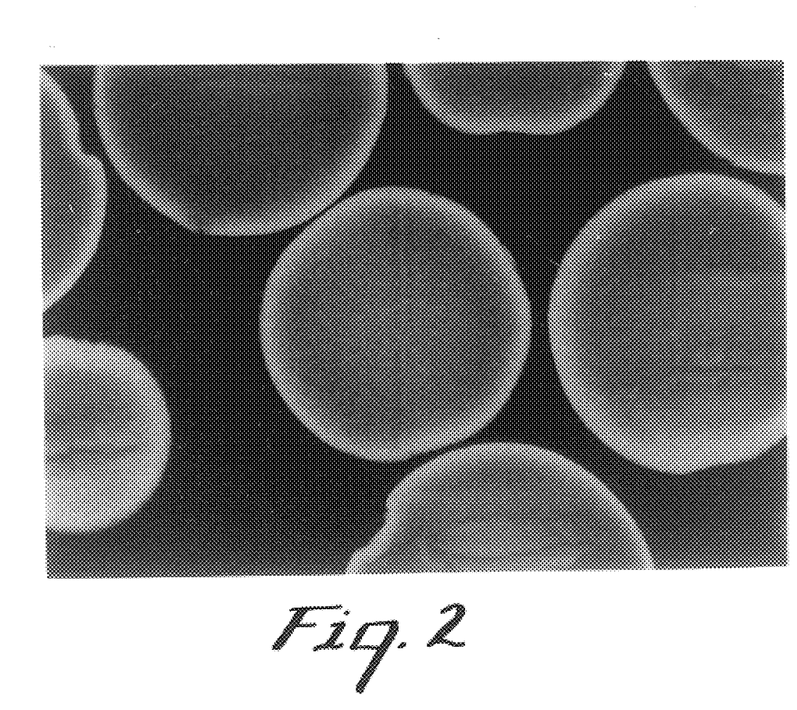
FIG. 2 is a fluorescence micrograph of a derivatized porous support, shown in cross-section, produced according to the present invention, that shows a more even distribution of Protein A ligand coupled throughout all surfaces of the support, enhancing functional efficiency.

FIGS. 1 and 2 provide a direct comparison of the the advantages of the present invention.

FIG. 1 is a comparison fluorescence micrograph of cross-sections of a derivatized porous support produced according to a method used in the prior art and identified in Comparison Example 6 below, where there is no attempt to provide a two step reaction of diffusion and then coupling. The cross-section shows an uneven distribution of ligand coupled at outer surfaces of the support. This is evidence of overcrowding that the method of the present invention avoids.

FIG. 2 is a fluorescence micrograph of cross-sections of a derivatized porous support produced according to the method of present invention and specifically according to Example 7 below where there was a change in pH between the diffusion step and the coupling step. Throughout the porous cross-section of the bead, a significantly more even distribution of ligand coupled throughout all surfaces of the support is found. With a molecular sparcity of coupled ligand at the outer surfaces, and a distribution of coupled ligand throughout all surfaces of a porous support, an optimum of coupling is achieved.

As seen in a comparison of FIGS. 1 and 2, a more uniform spatial distribution of coupled ligand is achieved such that at least 30% of ligand is coupled to internal surfaces within 70% of the geometric center of the support. Thus, the method of the present invention provides a controllable, more uniform spatial distribution of coupling of the ligand to the porous support.

Derivatized porous supports of the present invention have a sparcity of coupling of the ligand to outer surfaces of the porous support and have an enhanced coupling of the ligand to inner surfaces of the porous support.

Functional efficiency of coupled ligand can increase as much as 1.1 to 10 fold using the method of the present invention over functional efficiency achieved using prior methods. As such an unexpectedly superior derivatized support is achieved.

Figure 3:
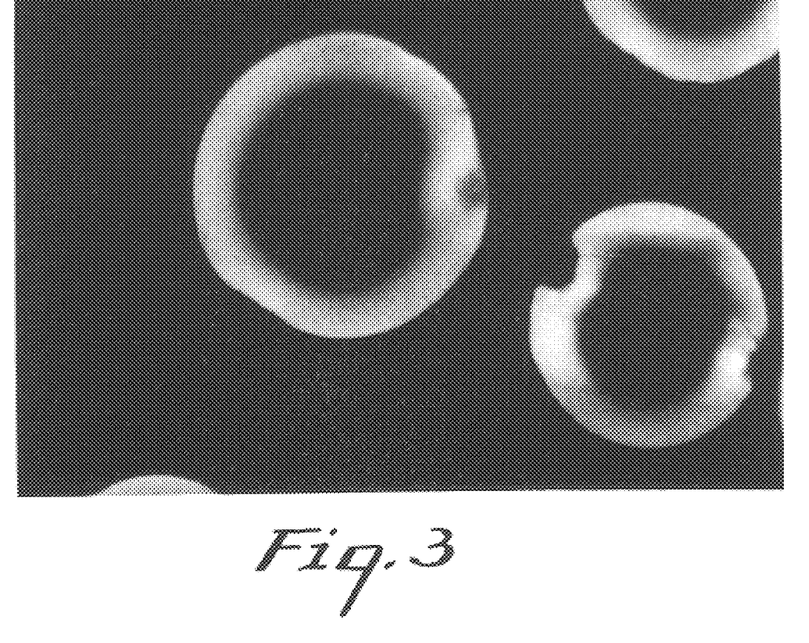
FIG. 3 is a comparison fluorescence micrograph of the same derivatized porous support as in FIG. 1, shown in cross-section, that shows an uneven distribution of immunoglobulin bound to the Protein A principally at outer surfaces of the support, demonstrating an undesired "halo effect" for functional efficiency.

FIG. 3 is a comparison fluorescence micrograph of cross-sections of a derivatized porous support shown in FIG. 1 with binding of immunoglobulin, produced according to a method used in the prior art and identified in Comparison Example 8 below. The cross-section shows an uneven distribution of ligate binding to ligand coupled at outer surfaces of the support. This is evidence of restricted diffusion and steric effects that demonstrates the "halo effect" of inadequate functional efficiency.

Figure 4:
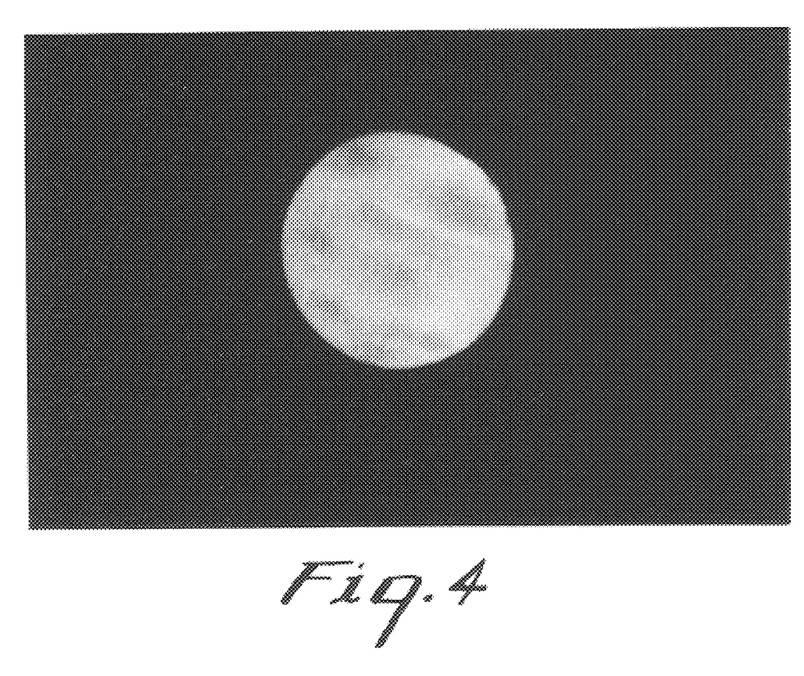
FIG. 4 is a fluorescence micrograph of the same derivatized porous support as in FIG. 2, shown in cross-section, that shows a more even binding of immunoglobulin to Protein A ligand coupled throughout all surfaces of the support, proving enhanced functional efficiency.

FIG. 4 is a fluorescence micrograph of cross-sections of a derivatized porous support shown in FIG. 2, produced according to the method of present invention and specifically according to Example 9 below where there was a ligate binding more uniformly throughout the bead and an avoidance of restricted diffusion and steric effect. Throughout the porous cross-section of the bead, a significantly more even distribution of ligate bound to coupled ligand throughout all surfaces of the support is found. With binding of ligate distributed on coupled ligand throughout all surfaces of a porous support, an optimum of functional efficiency is achieved.

For a greater understanding of the scope of the invention, the following examples are provided.

EXAMPLES

Comparison Example 1

This example describes the coupling of Protein A to Emphaze™ Biosupport Medium ABI using a one step method of the prior art. To triplicate 15 ml screw capped polypropylene tubes containing 50 milligrams each of dry Emphaze™ beads (Minnesota Mining and Manufacturing Company, St. Paul, Minn.) 2.5 milliliters of a solution of natural Protein A (Fermentech, Ltd., Edinburgh, UK) at 1.6 milligrams per milliliter in 1.2 M $Na_2SO_4$, 0.1 M $NaH_2PO_4$ pH 7.5 was added and mixed to wet all of the dry beads. The reaction mixture was then agitated by end-over-end rotation for a total of 75 minutes at room temperature. After centrifugation at 1200×g for 10 minutes, the supernatant was removed and analyzed for remaining Protein A by colorimetric analysis (BCA method from Pierce Chemical Company, Rockford, Ill.). The amount of Protein A coupled and the efficiency of coupling was determined by a difference calculation. The results of the coupling are shown in Table A. The beads were quenched with 4.0 milliliters of 3 M ethanol amine at pH 9.0 for about 18 hours (overnight). The beads from the combined triplicates were then sequentially washed with phosphate buffered saline (PBS: 0.025 M $NaH_2PO_4$, 0.15 M NaCl pH 7.4), 0.2 M sodium acetate pH 5.0, 0.5 M sodium bicarbonate pH 8.5, and PBS on a sintered glass fritted funnel (porosity D) using 20–30 volumes of each solution.

The washed beads were then tested for their immunoglobulin binding capacity by packing them into a 3×50 mm Omni glass column and running a chromatogram with purified human IgG (Sigma Chemical Company, St. Louis, Mo.) as the test solution. A total of 48 milligrams (16 milliliters of 3 milligrams per milliliter in 0.01 M $NaH_2PO_4$ pH 7.5) was loaded at a flow rate of 0.57 milliliters per minute followed by a wash of 6.8 milliliters of loading buffer, 6.8 milliliters of 2 M NaCl, 0.01 M $NaH_2PO_4$ pH 7.5, 4.6 milliliters of loading buffer, and the bound IgG was eluted with 4.6 milliliters of 0.1 M glycine, 2% acetic acid pH 2.2. Elution fractions were collected and the amount of IgG present determined by absorbance at 280 nm. The results for these beads is shown in Table A.

Comparison Example 2

This example describes the coupling of Protein A to Emphaze beads in a manner similar to that of Comparison Example 1 according to the prior art with the exception that the coupling solution contains a coupling competitor, 0.5 M Tris(hydroxymethyl)aminomethane (TRIS) in addition to sodium sulfate and phosphate buffer at pH 7.5.

The results of the coupling and the IgG capacity evaluation (as described in Comparison Example 1) are shown in Table A.

Example 3

This example describes a two step method of the present invention of coupling Protein A to Emphaze beads as a direct comparison to Comparison Example 1. Thus, the final solution conditions are the same as those of comparison Example 1 but there is a different ionic strength of the reaction mixture during the first step. In the second step the ionic strength of the reaction mixture is increased. To triplicate 50 milligram samples of dry Emphaze beads in 15 milliliter screw capped polypropylene tubes 0.5 milliliters of Protein A solution (8 milligrams per milliliter in 0.05 M $NaH_2PO_4$) was added at room temperature and allowed to hydrate the beads for 15 minutes. Then in a second step 2.0 milliliters of 1.5 M $Na_2SO_4$ 0.125 M $NaH_2SO_4$ pH 7.5 was added and the reaction continued with agitation as in Example 1 for an additional 60 minutes. The coupling analysis and IgG capacity were carried out as in Comparison Example 1 and the results are shown in Table A.

Example 4

This example describes the coupling of Protein A to Emphaze beads using a two step method of the present invention as a direct comparison to Comparison Example 2. In the second step, the ionic strength of the reaction mixture is increased, a coupling competitor that quenches azlactone is added, and the pH is increased. The method is similar to that of Example 3 with the exceptions that the Protein A is in 0.05 M sodium acetate pH 5.0 and the solution added in the second step contains 0.5 M TRIS in addition to the sodium sulfate and phosphate buffer at pH 7.5. The Protein A coupling and IgG binding capacities were determined as in Comparison Example 1 and those results are shown in Table A.

Comparison Example 5

This example describes the coupling of Protein A to Emphaze beads using a two step method of the present invention where only the pH changes between the first and second step. This is a comparison example because it shows that use of a different pH from that of Examples 3 and 4, and a change in pH alone from the first step to the second step does not work for the ligand Protein A. The method is similar to that of Example 3 with the exception that the Protein A was in 0.05 M sodium acetate pH 5.0 and the second step uses 0.125 M boric acid solution pH 9.5. Protein A coupling was determined as in Comparison Example 1 and the results are shown in Table A.

TABLE A

Results of Protein A Coupling to Emphaze Beads

| Example | Protein A Coupled (mg/ml) | Coupling Efficiency (%) | IgG Capacity (mg/ml) | Functional Efficiency (IgG/PA) |
|---|---|---|---|---|
| 1 | 10.3 (0.2) | 99.0 | 24.0 | 2.44 |
| 2 | 9.4 (0.2) | 97.9 | 26.2 | 2.43 |
| 3 | 9.7 (0.1) | 99.2 | 29.1 | 2.99 |
| 4 | 9.9 (0.1) | 98.6 | 38.3 | 3.96 |
| 5 | 0.0 | 0.0 | | |

The functional efficiency of both two step methods (Examples 3 and 4) of the present invention increased when compared with the one step methods of the prior art (Comparison Examples 1 and 2, respectively). The increases range from 22%–62%. There is also an additive effect of an increase in ionic strength and addition of an azlactone quencher in the second step. That increase is 32%.

Comparison Example 6 and Example 7

These examples describe the preparation of Emphaze beads coupled to fluorescently labeled Protein A for use in determining the distribution of the protein that results from different coupling methods according to the prior art for Comparison Example 6 and according to the present invention for Example 7. Protein A was tagged with Texas Red (Sigma Chemical Company) by the method of Titus et. al. in J. Immunological Methods 50, 193–204 (1982) such that a solution of 5 mg/ml in PBS resulted. This was mixed with a unlabeled Protein A such that a final concentration of 25 mg/ml resulted. This solution was then diluted for coupling to Emphaze beads according to the method as in Comparison Example 1 for Comparison Example 6 and according to the method as in Example 4 for Example 7 using 20 milligrams of beads and 1.0 milliliters of total solution. coupling efficiencies and the amounts of Protein A coupled (normalized to 1 ml of beads) were found to be essentially the same as those for the unlabeled Protein A in Comparison Example 1 and Example 4.

Samples of these beads were then cast in JB4-Plus embedding medium (PolySciences, Warrington, Pa.) and sectioned with a glass knife into sections about 4 microns in thickness. These were then mounted, examined under fluorescent conditions at a magnification of 500×, and photographed. FIGS. 1 and 2 show significantly different spatial distributions of the Protein A coupled to Emphaze beads. Since both preparations have the same total Protein A content, the "halo" distribution of Protein A in FIG. 1 (Comparison Example 6 beads) indicates that the ligand is concentrated into significantly less volume than the more uniform distribution of FIG. 2 (Example 7 beads). The Protein A is coupled to the bead in a manner that at least 70% of the amount of coupled Protein A is coupled to internal surfaces of the bead that are within 35% of the geometric center of the bead.

Comparison Example 8 and Example 9

These examples describe a method of determining the spatial distribution of fluorescently labeled human IgG bound to Emphaze beads with Protein A coupled. Aliquots of about 100 microliters of beads from Examples 1 and 4 were incubated with FITC-labeled human IgG (Sigma Chemical Company), about 1.5 milligrams in 0.5 milliliters of PBS, overnight at room temperature. The bead samples were then washed five times with 2.0 milliliters of PBS each to remove unbound antibody.

The beads were then prepared for microscopy as in Comparison Example 6 and Example 7. The photomicrographs of these beads can be seen in FIGS. 3 and 4 where the distributions of bound ligate are similar to the coupled ligand in FIGS. 1 and 2. This indicates that the more uniform distribution of Protein A ligand seen in FIG. 2 results in a more uniform distribution of bound IgG ligate (FIG. 4) and a higher capacity than the "halo" distribution of Protein A (FIGS. 1 and 3) and the lower IgG capacity of Comparison Example 1 beads. This also confirms that the method of coupling of the present invention can have an effect on the spatial distribution of ligand which can determine the functional efficiency of the resulting biologically active support. Thus, in this example where the support is a substantially spherical particle and the ligate is bound to ligand coupled to internal surfaces within a radius of 70% of the total radius of the particle. The ligand is coupled to the porous bead in a manner that has a percentage of permeation of coupled ligand of about 70% to the internal surfaces of a porous support.

Comparison Example 10

This example describes the coupling of Protein A to cyanogen bromide activated Sepharose branded agarose using a one step method of the prior art. CNBr-Activated Sepharose 4B (Pharmacia LKB, Biotechnology AB, Uppsala, Sweden) was prepared for reaction according to the manufacturer's instructions and aliquots of slurry equivalent to 0.6 milliliters of gel were placed into 15 milliliter screw capped polypropylene tubes. After removing the supernatant buffer solution, 3.75 milliliters of 1.0 milligrams of Protein A per milliliter in 0.5 M NaHCO$_3$ pH 8.5 was added and the mixture agitated by end-over-end rotation for a total of 75 minutes at room temperature. At that time the slurry was centrifuged at 1200×g for 5 minutes and the supernatant removed for determination of the amount of coupling of Protein A as in comparison Example 1. Results are shown in Table B. The gel was resuspended in 4.0 milliliters of 3 M ethanol amine pH 9.0 and agitated overnight (about 18 hours) at room temperature. The gel was then sequentially washed with PBS, 1 M NaCl in PBS and PBS using 8 milliliters of each solution.

These beads were then evaluated for the binding capacity of the coupled Protein A by the method of Comparison Example 1. Results are shown in Table B.

Comparison Example 11

This example describes the coupling of Protein A to cyanogen bromide activated Sepharose using a two step method where pH alone was adjusted from the first step to the second step. Slurry aliquots (0.6 milliliters) of CNBr-Activated Sepharose 4B were prepared as in Comparison Example 10 and reacted with 0.75 milliliters of 5.0 milligram Protein A per milliliter, and 0.05 M sodium acetate pH 5.0 at 4 degrees C. for 15 minutes. In a second step 3.0 milliliters of 0.625 M sodium bicarbonate pH 8.5 was added and the reaction mixture agitated by end-over-end rotation at room temperature for an additional 60 minutes. The mixture was then treated as in Comparison Example 10 to determine the amount of Protein A coupled and its binding capacity. Results are shown in Table B.

Comparison Example 12

This example describes the coupling of Protein A to cyanogen bromide activated Sepharose using a one step method of the prior art similar to that of Comparison Example 10 with the exception that the coupling solution contained 1.0 M $Na_2SO_4$, 0.5 M $NaHCO_3$ pH 8.5. Protein A coupling results and binding capacities were determined as in Comparison Example 1 and are shown in Table B.

Example 13

This example describes the coupling of Protein A to cyanogen bromide activated Sepharose using a two step method of the present invention similar to that of Example 11 with the exception that the solution used in the second step contained 1.25 M $Na_2SO_4$, 0.625 M $NaHCO_3$ pH 8.5. Protein A coupling results and binding capacities were determined as in Comparison Example 1 and are shown in Table B.

Example 14

This example describes the coupling of Protein A to cyanogen bromide activated Sepharose using a one step method similar to that of Comparison Example 10 with the exception that the coupling solution contained 1.0 M $Na_2SO_4$, 0.5 M $NaHCO_3$, 0.4 M TRIS pH 8.5. Protein A coupling results and binding capacities were determined as in Comparison Example 1 and are shown in Table B.

Example 15

This example describes the coupling of Protein A to cyanogen bromide activated Sepharose using a two step method of the present invention similar to that of Comparison Example 11 with the exception that the solution used in the second step contained 1.25 M $Na_2SO_4$, 0.625 M $NaHCO_3$, 0.5 M TRIS pH 8.5. Protein A coupling results and binding capacities were determined as in Comparison Example 1 and are shown in Table B.

TABLE B

Results of Protein A Coupling to CNBr-Activated Beads

| Example | Protein A Coupled (mg/ml) | Coupling Efficiency (%) | IgG Capacity (mg/ml) | Functional Efficiency (IgG/PA) |
| --- | --- | --- | --- | --- |
| 10 | 5.6 | 89.6 | 31.0 | 5.54 |
| 11 | 5.6 | 89.6 | 30.9 | 5.52 |
| 12 | 5.9 | 100.0 | 34.8 | 5.90 |
| 13 | 5.9 | 100.0 | 37.4 | 6.34 |
| 14 | 2.8 | 48.3 | 19.4 | 6.93 |
| 15 | 4.0 | 69.0 | 31.1 | 7.78 |

Functional efficiency increases for the two step methods (Examples 13 and 15) when individually compared to their one step counterparts (Comparison Examples 12 and 14, respectively). The functional efficiency increases for Examples 13 and 15 are 7% and 12%, respectively, over Comparison Examples 12 and 14. These two step methods of the present invention also can be seen to produce a superior result to coupling under the manufacturer's recommended conditions with either a one or two step method (Comparison Examples 10 and 11). The coupling efficiency of the one step method with TRIS present (Comparison Example 14) is significantly less than the two step method with TRIS present (Example 15), but both are less than the other examples of coupling Protein A to CNBr-Activated Sepharose 4B even though functional efficiency is greater from Example 15 over Comparison Example 14.

Example 16

1 mg of 7D7B10-Mab (obtained from American National Red Cross) is incubated with 125 mg Emphaze™ beads at pH 4.0 and the solution is allowed to permeate the beads for 10 mins at 4° C. in the presence of 0.5M Tris. After the first 10 minute incubation with 0.5 M Tris, the salt concentration is raised to 0.8 M $Na_2SO_4$ at pH 4.0 and allowed to permeate the beads for 10 mins at 4° C. The pH is then increased to pH 9.0 with several drops of 1N NaOH. The reaction at pH 9.0 is allowed to proceed for 40 mins at 4° C. The total permeation/diffusion and reaction time is 60 mins at 4° C. The supernatant is pipetted off. Residual reactive sites are blocked with 4 ml of 1.0 M ethanolamine in 0.05 M sodium pyrophosphate, pH 9.3 for 30 mins at RT. Beads are allowed to settle and the supernatant is pipetted off. An additional 4 mls of blocking solution is combined with the beads and incubated for 60 mins at RT. Upon completion of the second blocking step, the beads are washed with four column volumes of 0.5 M NaCl and equilibrated with loading buffer for protein immunosorption. The 7D7B10-Mab coupling efficiency to the azlactone is greater than 70%. 0.07 or 0.7 mgs of recombinant human Protein C in 3 ml of 0.125 M Tris, 0.1 NaCl, 25 mM EDTA at pH 6.5 is loaded batchwise and eluted columnwise at a linear velocity of 1 cm/min into a 1.0 cm by 10.0 cm length glass chromatography column containing the 7D7B10-Mab:azlactone beads at 4° C. The protein C is eluted from the immunosorbent at 1 cm/min linear velocity with 4.0 ml of 0.125 M Tris, 0.1 NaCl, 25 mM $CaCl_2$ at pH 6.5. The immunosorbent functional efficiency is about 16%. The results of this Example 16 can be compared with the results of Comparison Example 5 (Protein A) where an adjustment of pH between the first and second steps did not yield coupling.

Example 17

10 mg of 7D7B10-Mab is incubated with 125 mg Emphaze™ beads at pH 4.0 and the solution is allowed to permeate the beads for 10 mins at 4° C. in the presence of 0.5M Tris. After the first 10 minute incubation with 0.5 M Tris, the salt concentration is raised to 0.8 M $Na_2SO_4$ at pH 4.0 and allowed to permeate the beads for 10 mins at 4° C. The pH is then increased to pH 9.0 with several drops of 1N NaOH. The reaction at pH 9.0 is allowed to proceed for 40 mins at 4° C. The total permeation/diffusion and reaction time is 60 mins at 4° C. The supernatant is pipetted off. Residual reactive sites are blocked with 4 ml of 1.0 M ethanolamine in 0.05 M sodium pyrophosphate, pH 9.3 for 30 mins at RT. Beads are allowed to settle and the supernatant is pipetted off. An additional 4 mls of blocking solution is combined with the beads and incubated for 60 mins at RT. Upon completion of the second blocking step, the beads are washed with four column volumes of 0.5 M NaCl and equilibrated with loading buffer for protein immunosorption. The 7D7B10-Mab coupling efficiency to the azlactone is greater than 70%. 0.07 or 0.7 mgs of recombinant human Protein C in 3 ml of 0.125 M Tris, 0.1 NaCl, 25 mM EDTA at pH 6.5 is loaded batchwise and eluted columnwise at a linear velocity of 1 cm/min into a 1.0 cm by 10.0 cm length glass chromatography column containing the 7D7B10-Mab:azlactone beads at 4° C. The protein C is eluted from the immunosorbent at 1 cm/min linear velocity with 4.0 ml of 0.125 M Tris, 0.1 NaCl, 25 mM $CaCl_2$ at pH 6.5. The immunosorbent functional efficiency is about 16%.

Example 18

1 mg of 7D7B10-Mab is incubated with 125 mg Emphaze™ beads at pH 4.0 for 10 mins at 4° C. in the presence of 0.5M Tris. After the first 10 minute incubation with 0.5 M Tris, the pH is then increased to pH 9.0 with several drops of 1N NaOH. The reaction at pH 9.0 is allowed to proceed for 50 mins at 4° C. The total permeation/diffusion and reaction time is 60 mins at 4° C. The supernatant is pipetted off. Residual reactive sites are blocked with 4 ml of 1.0 M ethanolamine in 0.05 M sodium pyrophosphate, pH 9.3 for 30 mins at RT. Beads are allowed to settle and the supernatant is pipetted off. The 7D7B10-Mab coupling efficency is greater than 50%. An additional 4 mls of blocking solution is combined with the beads and incubated for 60 mins at RT. Upon completion of the second blocking step, the beads are washed with four column volumes of 0.5 M NaCl and equilibrated with loading buffer for protein immunosorption. 0.07 or 0.7 mg of recombinant human Protein C in 2.0 ml of 0.125 M Tris, 0.1 NaCl, 25 mM EDTA at pH 6.5 is loaded batchwise and eluted columnwise at 1 cm/min linear velocity into a 1.0 cm by 10.0 cm length glass chromatography column containing the 7D7B10-Mab: azlactone beads at 4° C. The protein C is eluted from the immunosorbent at 1 cm/min linear velocity with 4.0 ml of 0.125 M Tris, 0.1 NaCl, 25 mM $CaCl_2$ at pH 6.5. The immunosorbent functional efficiency is about 14%.

Example 19

10 mg of 7D7B10-Mab is incubated with 125 mg azlactone beads at pH 4.0 for 10 mins at 4° C. in the presence of 0.5M Tris. After the first 10 minute incubation with 0.5 M Tris, the pH is then increased to pH 9.0 with several drops of 1N NaOH. The reaction at pH 9.0 is allowed to proceed for 50 mins at 4° C. The total permeation/diffusion and reaction time is 60 mins at 4° C. The supernatant is pipetted off. Residual reactive sites are blocked with 4 ml of 1.0 M ethanolamine in 0.05 M sodium pyrophosphate, pH 9.3 for 30 mins at RT. Beads are allowed to settle and the supernatant is pipetted off. The 7D7B10-Mab coupling efficency is greater than 50%. An additional 4 mls of blocking solution is combined with the beads and incubated for 60 mins at RT. Upon completion of the second blocking step, the beads are washed with four column volumes of 0.5 M NaCl and equilibrated with loading buffer for protein immunosorption. 0.07 or 0.7 mg of recombinant human Protein C in 2.0 ml of 0.125 M Tris, 0.1 NaCl, 25 mM EDTA at pH 6.5 is loaded batchwise and eluted columnwise at 1 cm/min linear velocity into a 1.0 cm by 10.0 cm length glass chromatography column containing the 7D7B10-Mab:azlactone beads at 4° C. The protein C is eluted from the immunosorbent at 1 cm/min linear velocity with 4.0 ml of 0.125 M Tris, 0.1 NaCl, 25 mM $CaCl_2$ at pH 6.5. The immunosorbent functional efficiency is 14%.

Example 20

20 mg of 12A8-Mab is incubated with 350 mg Emphaze™ beads at pH 4.0 for 10 mins at 4° C. in the presence of 0.5M Tris. After the first 10 minute incubation with 0.5 M Tris, the salt concentration is raised to 0.8 M $Na_2SO_4$ at pH 4.0 and allowed to permeate the beads for 10 mins at 4° C. The pH is then increased to pH 9.0 with several drops of 1N NaOH. The reaction at pH 9.0 is allowed to proceed for 40 mins at 4° C. The total permeation/diffusion and reaction time is 60 mins at 4° C. The supernatant is pipetted off. Residual reactive sites are blocked with 10 ml of 1.0 M ethanolamine in 0.05 M sodium pyrophosphate, pH 9.3 for 30 mins at RT. Beads are allowed to settle and the supernatant is pipetted off. The 12A8-Mab coupling efficency is greater than 70%. An additional 10 mls of blocking solution is combined with the beads and incubated for 60 mins at RT. Upon completion of the second blocking step, the beads are washed with four column volumes of 0.5 M NaCl and equilibrated with loading buffer for protein immunosorption. 3.0 mg of recombinant human Protein C in 30 ml of 0.125 M Tris, 0.1 NaCl, 25 mM EDTA at pH 6.5 is loaded columnwise at 1 cm/min linear velocity into a 1.0 cm by 10.0 cm length glass chromatography column containing the 12A8-Mab:azlactone beads at 4° C. The protein C is eluted from the immunosorbent at 1 cm/min linear velocity with 15.0 ml of 0.1 M $NaHCO_3$, 0.15 M NaCl at pH 10.0. The immunosorbent functional efficiency is 25%.

Example 21

750 mg of 12A8-Mab (obtained from the American National Red Cross) is incubated with 24 g azlactone beads at pH 4.0 for 10 mins at 4° C. in the presence of 0.5M Tris. After the first 10 minute incubation with 0.5 M Tris, the salt concentration is raised to 0.8 M $Na_2SO_4$ at pH 4.0 for 10 mins at 4° C. The pH is then increased to pH 9.0 dropwise with 1N NaOH. The reaction at pH 9.0 is allowed to proceed for 40 mins at 4° C. The total diffusion and reaction time is 60 mins at 4° C. The supernatant is pipetted off. Residual reactive sites are blocked with 240 ml of 1.0 M ethanolamine in 0.05 M sodium pyrophosphate, pH 9.3 for 30 mins at RT. Beads are allowed to settle and the supernatant is pipetted off. The 12A8-Mab coupling efficency is greater than 70%. An additional 240 mls of blocking solution is combined with the beads and incubated for 60 mins at RT. Upon completion of the second blocking step, the beads are washed with four column volumes of 0.5 M NaCl and equilibrated with loading buffer for protein immunosorption. 125 mg of recombinant human Protein C in 600 ml of 0.125 M Tris, 0.1 NaCl, 15 mM $MgCl_2$ at pH 8.0 is loaded columnwise at 1 cm/min linear velocity into a 5.0 cm by 50.0 cm length glass chromatography column containing the 12A8-Mab:azlactone beads at 4° C. The protein C is eluted from the immunosorbent at 1 cm/min linear velocity with 210 ml of 0.1M NaHCO$_3$, 0.15 M NaCl at pH 10.0. The immunosorbent functional efficiency is 25%.

While embodiments have been identified and exemplified, the following claims and their equivalents provide the scope of the present invention.

What is claimed is:

1. A method for coupling a biologically active ligand within a porous support comprising:
   (a) diffusing a biologically active ligand into a porous support; and
   (b) altering conditions to provide rapid covalent coupling of the biologically active ligand to the porous support;
      wherein a rate of ligand coupling during step (a) is less than a rate of ligand coupling and a quantity of ligand coupled during step (b); and
      wherein the step of altering conditions comprises increasing pH, increasing ionic concentration, or increasing temperature, or combinations thereof;
   wherein the biological activity of coupled ligand is retained.

2. The method of claim 1 wherein the biologically active ligand is selected from the group consisting of proteins, peptides, polypeptides, antibodies, antigenic substances, enzymes, cofactors, lectins, hormones, hormone receptors, coagulation factors, histones, vitamins, and cell surface markers.

3. The method of claim 1 wherein the conditions of step (a) are caused to prevail over a lesser period than those of step (b).

4. The method of claim 1 wherein the coupling conditions of step (b) are such that the coupled ligand retains its biological activity.

5. The method of claim 4 wherein the coupling conditions of step (b) further comprise adding a coupling competitor.

6. The method of claim 5 wherein the concentration of coupling competitor ranges from 0.1M to 10M.

7. The method of claim 1 wherein pH of step (a) is less than pH of step (b).

8. The method of claim 7 wherein the coupling conditions of step (b) further comprise adding polyanionic salts for coupling of the ligand to the porous support.

9. The method of claim 7 wherein, for step (a), the pH ranges from about 3 to about 7.

10. The method of claim 7 wherein the pH, for step (b), ranges from about 7 to about 10.

11. The method of claim 7 wherein ionic concentration in step (a) is less than ionic concentration in step (b).

12. The method of claim 11 wherein in step (b), sufficient coupling competitor is added to permit the coupled ligand to retain its biological activity.

13. The method of claim 12, wherein the concentration of coupling competitor ranges from 0.1M to 10M.

14. The method of claim 11 wherein the change in ionic concentration from step (a) to step (b) ranges from about 0.5 M to about 1.5M.

15. The method of claim 1 wherein ionic concentration in step (a) is less than ionic concentration in step (b).

16. The method of claim 15 wherein the change in ionic concentration from step (a) to step (b) ranges from about 0.5 M to about 1.5M.

17. The method of claim 1 wherein step (a) has a lower Thiele modulus than step (b).

18. The method of claim 1 wherein the temperature of step (a) is less than the temperature of step (b).

19. The method of claim 18 wherein the change in temperature from step (a) to step (b) ranges from about 10° C. to about 35° C.

20. The method of claim 1 wherein the method effects a uniform spatial distribution of the ligand coupled to the porous support.

21. The method of claim 1 wherein the porous support has internal and external surfaces and further has a reactive functional group at sites on both of said internal and external surfaces and wherein the method effects substantially uniform covalent coupling of the ligand to said reactive functional group sites at both internal and external surfaces of the porous support.

22. The method of claim 21 wherein the reactive functional group is an electrophile.

23. The method of claim 1 wherein the porous support is azlactone-functional.

24. A method for coupling a monoclonal antibody within a porous support comprising:
   (a) diffusing a monoclonal antibody into a porous support; and
   (b) altering conditions to provide rapid covalent coupling of the monoclonal antibody to the porous support;
      wherein a rate of antibody coupling and a quantity of antibody coupled during step (a) is less than a rate of antibody coupling and a quantity of antibody coupled during step (b); and
      wherein the step of altering conditions comprises increasing pH, increasing ionic concentration, or increasing temperature, or combinations thereof.

25. A derivatized porous support produced according to the method of claim 24 wherein the porous support is azlactone-functional.

26. A method for coupling a nucleophilic ligand within a porous support comprising:
   (a) diffusing a nucleophilic ligand into a porous support; and
   (b) altering conditions to provide rapid covalent coupling of the nucleophilic ligand to the porous support;
      wherein a rate of ligand coupling during step (a) is less than a rate of ligand coupling and a quantity of ligand coupled during step (b); and
      wherein the step of altering conditions comprises increasing pH, increasing ionic concentration, or increasing temperature, or combinations thereof.

27. The method of claim 26 wherein the ligand is biologically active and in step (b) the coupled ligand retains its biological activity.

28. The method of claim 27 wherein step (b) further comprises adding a coupling competitor.

29. The method of claim 28 wherein the concentration of coupling competitor ranges from 0.1M to 10M.

30. The method of claim 26 wherein pH of step (a) is less than pH of step (b).

31. The method of claim 30 wherein step (b) further comprises adding polyanionic salts for coupling of the ligand to the porous support.

32. The method of claim 30, wherein for step (a), the pH ranges from about 3 to about 7.

33. The method of claim 30 wherein the pH, for step (b), ranges from about 7 to about 10.

34. The method of claim 30 wherein ionic concentration in step (a) is less than ionic concentration in step (b).

35. The method of claim 34 wherein the ligand has biological activity and in step (b) sufficient coupling competitor is added to permit the coupled ligand to retain its biological activity.

36. The method of claim 35, wherein the concentration of coupling competitor ranges from 0.1M to 10M.

37. The method of claim 34 wherein the change in ionic concentration from step (a) to step (b) ranges from about 0.5 M to about 1.5M.

38. The method of claim 26 wherein ionic concentration of step (a) is less than ionic concentration of step (b).

39. The method of claim 38 wherein the change in ionic concentration from step (a) to step (b) ranges from about 0.5 M to about 1.5M.

40. The method of claim 26 wherein the nucleophilic ligand is a monoclonal antibody.

41. A derivatized porous support produced according to the method of claim 40 wherein the porous support is azlactone-functional.

42. The method of claim 26 wherein the temperature of step (a) is less than the temperature of step (b).

43. The method of claim 42 wherein the change in temperature from step (a) to step (b) ranges from about 10° C. to about 35° C.

44. The method of claim 26 wherein the method effects a uniform spatial distribution of the ligand coupled to the porous support.

45. The method of claim 26 wherein the porous support has internal and external surfaces and further has a reactive functional group at sites on both of said internal and external surfaces and wherein the method effects substantially uniform covalent coupling of the ligand to said reactive functional group sites at both internal and external surfaces of the porous support.

46. The method of claim 45 wherein the reactive functional group is an electrophile.

47. The method of claim 26 wherein the porous support is azlactone-functional.

48. The method of claim 26 wherein step (a) has a lower Thiele modulus than step (b).

49. A method for coupling a nucleophilic ligand within a porous support comprising:
   (a) diffusing a nucleophilic ligand into a porous support; and
   (b) altering conditions to provide rapid covalent coupling of the ligand to the porous support before unbound ligand vacates the desired location for coupling;
      wherein a rate of ligand coupling during step (a) is less than a rate of ligand coupling and a quantity of ligand coupled during step (b); and
      wherein the step of altering conditions comprises increasing pH, increasing ionic concentration, or increasing temperature, or combinations thereof.

50. The method of claim 49 wherein the ligand is a monoclonal antibody.

51. A monoclonal antibody internally coupled-derivatized porous support comprising a porous support to which an amount of a monoclonal antibody is coupled; wherein, of the amount of coupled monoclonal antibody, at least 30% of the amount is coupled to internal surfaces within 70% of the geometric center of the support; provided that amount of monoclonal antibody coupled to internal surfaces retains its biological activity.

52. The porous support of claim 51 wherein the support is azlactone-functional.

53. The derivatized porous support of claim 51, wherein a protein is bound with a ratio of bound protein/antibody of greater than about 20% at a molar ratio of 2:1 of protein to antibody.

54. The derivatized porous support according to claim 51 wherein the support is substantially spherical.

55. The derivatized porous support according to claim 54 wherein the internal electrophilic functionalities that are within 70% of the geometric center of the support are located within an area of the sphere that is within 70% of the radius of the sphere as measured from the center of the sphere.

56. A method of increasing the functional efficiency of a separation method wherein a ligate is to be bound to a nucleophilic, biologically active ligand that is covalently bound to a porous support, comprising effecting improved spatial distribution of said ligand throughout said porous support by:
   (a) diffusing said ligand into said porous support;
   (b) altering conditions to provide rapid covalent coupling of said ligand to said porous support;
      wherein a rate of ligand coupling and a quantity of ligand coupled during step (a) is less than a rate of ligand coupling and a quantity of ligand coupled during step (b); and
      wherein the step of altering conditions comprises increasing pH, increasing ionic concentration, or increasing temperature, or combinations thereof; and
   (c) contacting said ligand with said ligate,
      wherein biological activity of the coupled ligand is retained.

57. The method of claim 56 wherein the ligand is a monoclonal antibody.

* * * * *